United States Patent [19]

Knight et al.

[11] Patent Number: 5,290,308
[45] Date of Patent: Mar. 1, 1994

[54] ENDOSCOPIC INSTRUMENT

[75] Inventors: David A. Knight; Bahram B. Rahimzadeh, both of Durham, N.C.

[73] Assignee: Edward Weck Incorporated, Research Triangle Park, N.C.

[21] Appl. No.: 913,852

[22] Filed: Jul. 15, 1992

[51] Int. Cl.$^5$ ............................................. A61B 17/10
[52] U.S. Cl. .................................... 606/205; 604/247; 606/174; 606/207
[58] Field of Search ................... 604/22, 33, 247, 249; 606/142, 167, 170, 174, 175, 205–209; 128/751–755

[56] References Cited

U.S. PATENT DOCUMENTS

| | | |
|---|---|---|
| 2,691,370 | 10/1954 | Wallace . |
| 3,618,611 | 11/1971 | Urban ............................ 606/170 |
| 3,964,468 | 6/1976 | Schulz ............................ 128/751 |
| 4,440,170 | 4/1984 | Golden et al. ............... 606/142 |
| 4,598,698 | 7/1986 | Siegmund . |
| 4,646,751 | 3/1987 | Maslanka . |
| 4,674,501 | 6/1987 | Greenberg ................... 606/142 |
| 4,750,477 | 6/1988 | Wardle . |
| 4,800,869 | 1/1989 | Nakajima ........................ 128/4 |
| 4,872,456 | 10/1989 | Hasson ........................... 606/207 |
| 4,919,152 | 4/1990 | Ger ................................. 606/142 |
| 4,994,024 | 2/1991 | Falk ................................ 604/22 |
| 5,037,386 | 8/1991 | Marcus et al. . |
| 5,049,128 | 9/1991 | Duquette ........................ 604/83 |
| 5,147,378 | 9/1992 | Markham ...................... 606/206 |

FOREIGN PATENT DOCUMENTS 2119696 11/1983 United Kingdom ............... 606/208

*Primary Examiner*—Ralph Lewis
*Attorney, Agent, or Firm*—Rosenblatt & Associates

[57] ABSTRACT

The present invention is a lightweight endoscopic instrument which has a flushing port with a check valve assembly therein. The check valve retains carbon dioxide which is used during endoscopic procedures. Upon removal of the instrument, a pressurized fluid can be connected to the flush port, with internal seals directing the pressurized fluid through an annular space between the stem of the instrument and a central actuating rod or element so that any tissue or blood which may have entered into such annular space is flushed out the distal end of the instrument. The instrument features a knob allowing it to rotate on its longitudinal axis while having a handle that can be held in a fixed position by the surgeon. An index mechanism is provided to audibly and/or visually give an indication at preset increments of rotation. The instrument is lightweight to decrease fatigue and is simply and economically constructed.

14 Claims, 3 Drawing Sheets

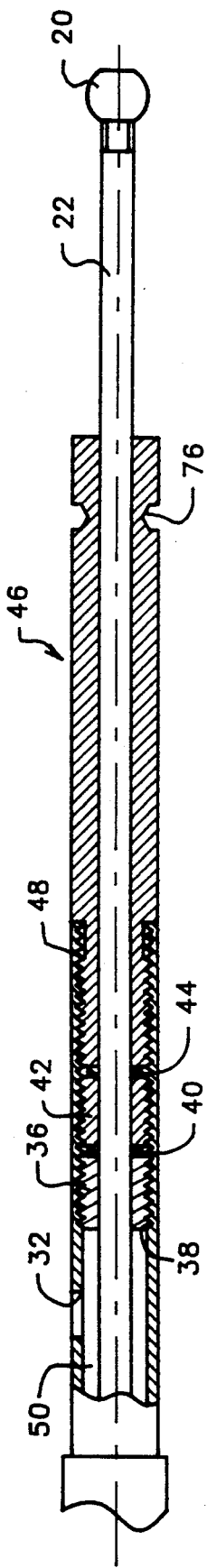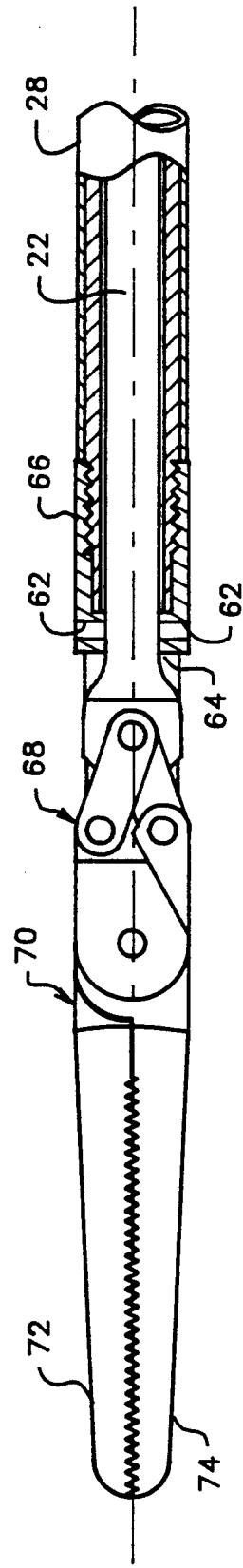
FIG. 3
FIG. 4

ENDOSCOPIC INSTRUMENT

FIELD OF THE INVENTION

The field of this invention is endoscopic instruments.

BACKGROUND OF THE INVENTION

Endoscopic procedures have become more and more common. A host of specialty instruments designed for endoscopic procedures have been developed. These instruments typically are elongated and controlled at their proximal end by the surgeon. Remotely, at the distal end, can be mounted a variety of different instrument assemblies to facilitate such activities as cutting, gripping, or cauterizing, to name a few. Common in many such instruments is an elongated housing or stem, with some operating mechanism, such as a rod or a wire, extending therethrough to the distal end of the instrument. Frequently at the distal end, the annular space between the housing or stem and the operating mechanism leaves portions exposed where blood or tissue can migrate into the annular space. This is undesirable since endoscopic tools are reused, perhaps several times in the same day on different patients. It is desirable to be able to completely sterilize these instruments between procedures. This includes getting into the annular space between the housing or stem and the rod or other device that extends therethrough. At the same time it is desirable to have the instrument be as compact and lightweight as possible to facilitate placement of the distal end within the body and to minimize fatigue for the surgeon handling the instrument at the proximal end. Many times during a procedure, the instrument must be rotated about its own axis for better placement. Accordingly, it is not only desirable to have a lightweight structure, but also a mechanism for rapidly changing the orientation of the assembly at the distal end to facilitate the endoscopic procedure. At the same time, the instrument must be constructed in a manner that does not allow the gasses typically used in endoscopic procedures, such as carbon dioxide, to escape from the area being worked on, thus obstructing the surgeon's view. In the past, bulky arthroscopic cannulas with fluid passages have been designed such as shown in U.S. Pat. No. 5,037,386. Instruments have been designed with means to add an irrigating fluid such as shown in U.S. Pat. No. 4,754,077. Other diagnostic devices have been fairly bulky and provide for injection of a fluid or a gas during operating. Such a device is illustrated in U.S. Pat. No. 4,598,698. Flexible biopsy forceps, with a cleaning port for introducing cleansing fluid, are illustrated in U.S. Pat. No. 4,646,751. U.S. Pat. No. 2,691,370 illustrates an instrument for heart surgery involving a telescope therein with means for flushing the front lens of the telescope during heart surgery.

SUMMARY OF THE INVENTION

The present invention is a lightweight endoscopic instrument which has a flushing port with a check valve assembly therein. The check valve retains carbon dioxide which is used during endoscopic procedures. Upon removal of the instrument, a pressurized fluid can be connected to the flush port, with internal seals directing the pressurized fluid through an annular space between the stem of the instrument and a central actuating rod or element so that any tissue or blood which may have entered into such annular space is flushed out the distal end of the instrument. The instrument features a knob allowing it to rotate on its longitudinal axis while having a handle that can be held in a fixed position by the surgeon. An index mechanism is provided to audibly and/or visually give an indication at preset increments of rotation. The instrument is lightweight to decrease fatigue and is simply and economically constructed.

BRIEF DESCRIPTION OF THE DRAWINGS

FIG. 3 is a further detailed view of the proximal end of the instrument, illustrating the seal assembly inside the stem.

FIG. 4 is a detailed view of the distal end of the instrument, showing a jaw assembly as one of several types of devices that can be placed at the distal end of such an instrument.

DETAILED DESCRIPTION OF THE PREFERRED EMBODIMENT

Figure 1:
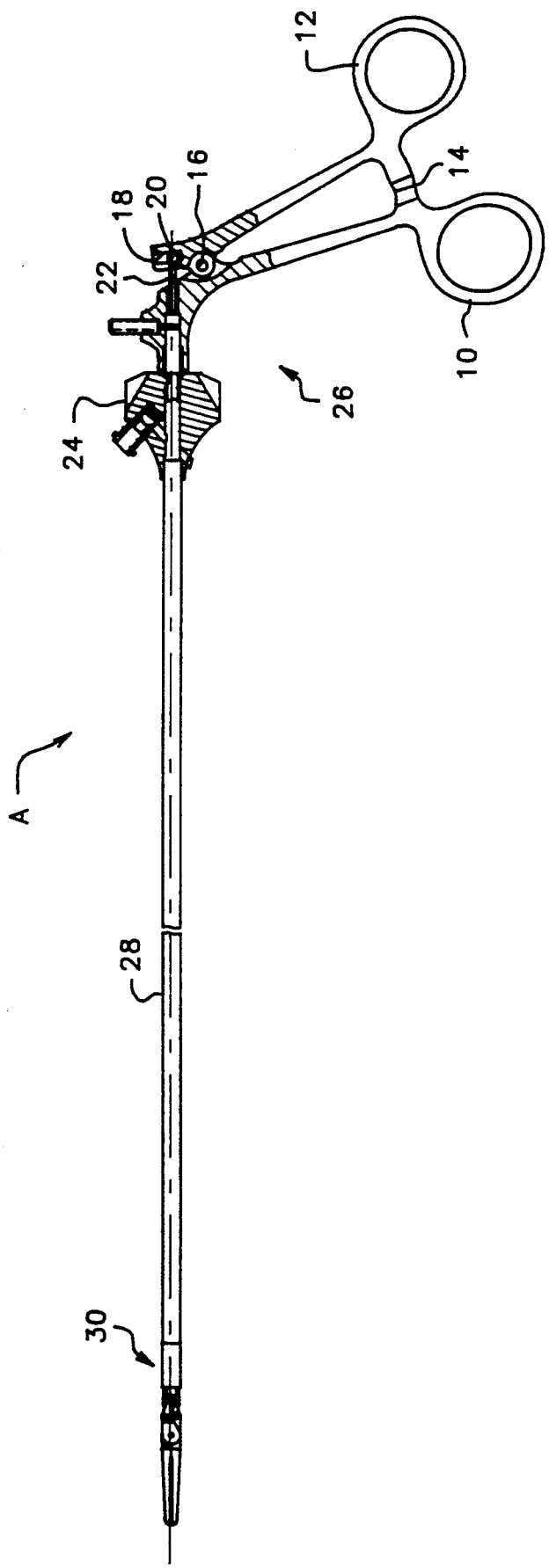
FIG. 1 is a sectional elevational view of the instrument.

The apparatus A is illustrated in FIG. 1. It is adaptable for actuation with one hand through handles 10 and 12. The relative position of handles 10 and 12 can be selectively held through detent 14, which can be adjusted by varying the amount of pressure applied to handles 10 and 12. Handles 10 and 12 are pinned together at pin 16. Handle 12 has a recess 18 to accept a ball 20, which is connected to rod 22. By bringing handles 10 and 12 closer to each other, ball 20 is pulled away from knob 24, thus translating the rod 22 toward the proximal end 26 of the apparatus A. Knob 24 is fixedly mounted to stem assembly 28. Stem assembly 28 extends to the distal end 30 of the apparatus A. Stem Assembly 28 must have some flexibility and preferably have good torsional strength to facilitate precise rotation of an instrument mounted to its distal end, such as jaw 70, by virtue of a like rotation to knob 24. In the annular space 50 between stem assembly 28 and rod 22, there are several sealing components illustrated in FIG. 3. As shown in FIG. 3, the stem assembly 28 has a port 32, which is in line with bore 34 (see FIG. 2), when the apparatus A is assembled. Bore 34 is normally plugged 35 at the bottom. The bore 34 extends through knob 24 to facilitate manufacturing. Bore 34 could be angled in other directions such as towards the proximal end 26. Proximally to port 32 and in the annular space 50 between rod 22 and stem assembly 28 are several components starting with a set screw or backup member 36. Set screw 36 engages internal threads 38 on stem assembly 28, and due to the nature of such threads, reaches a fixed position. Once the set screw 36 has been set in place, a washer 40, a seal (preferably Teflon ®) 42, and another washer 44 are all placed within stem assembly 28 resting on set screw 36. To complete the assembly, a detented capture 46, which has a threaded end 48, is threaded into threads 38. The capture 46 compresses seal 42 between washers 40 and 44, effectively creating a seal of the annular space 50 between rod 22 and stem assembly 28.

In knob 24 is a ball check 52, which includes a spring 54, a ball 56, and a seat 58. Bore 34 is blocked off by ball 56 due to the action of spring 54. Accordingly, when the apparatus A is in use and carbon dioxide gas is used during the endoscopic procedure, gas that migrates into annulus 50 will be contained therein due to seal 42 and ball 56 sealingly in contact with seat 58.

When it is desired to clean the apparatus A, a fluid pressure source (not shown) can be connected to fitting 60, which can be a Luer Lock or equivalent. Application of pressure from the pressure source (not shown) to fitting 60 displaces ball 56 away from seat 58 and allows flow into bore 34 and down annulus 50. Optionally, lateral ports 62 (see FIG. 4), which are fairly small, usually about 0.015 inch, may also be used to facilitate flow down annulus 50. The flush fluid escapes axially along rod 22 through a clearance 64 between the jaw holder 66 and rod 22. Jaw holder 66 is a fitting attached to the end of stem assembly 28 to engage a portion of linkage 68 in the embodiment shown in FIG. 4.

While many different types of instruments can be placed at the end of rod 22, such as scissors, needle holders, dissectors, forceps, graspers, or retractors, and rod 22 itself can be made of a variety of different materials, the particular instrument mounted at the distal end of the apparatus A shown in FIG. 4 is a jaw assembly 70, which is connected to rod 22 through linkage 68. The jaw assembly 70 features a pair of jaws 72 and 74 which move away from each other or towards each other, depending upon movement of rod 22. The jaw assembly 70 through linkage 68 also bears on jaw holder 66. Accordingly, bringing handles 10 and 12 together results in pulling back on rod 22 with a proximal pull on linkage 68. Since portions of linkage 68 bear on jaw holder 66, the linkage 68 is actuated to spread the jaws 72 and 74.

At times it may be desirable to reorient the instrument mounted to the distal end of rod 22. In the apparatus A this is accomplished by rotation of knob 24. Rotation of knob 24 results in rotation of stem assembly 28. Since stem assembly 28 is connected to linkage 68 at jaw holder 66, the linkage 68 turns the same amount of rotation as is applied to knob 24. Since linkage 68 is connected to rod 22, rod 22 also turns the same amount of rotation applied to knob 24. Rob 22 is free to rotate because the mounting ball 20 is rotatably connected to recess 18.

Figure 2:
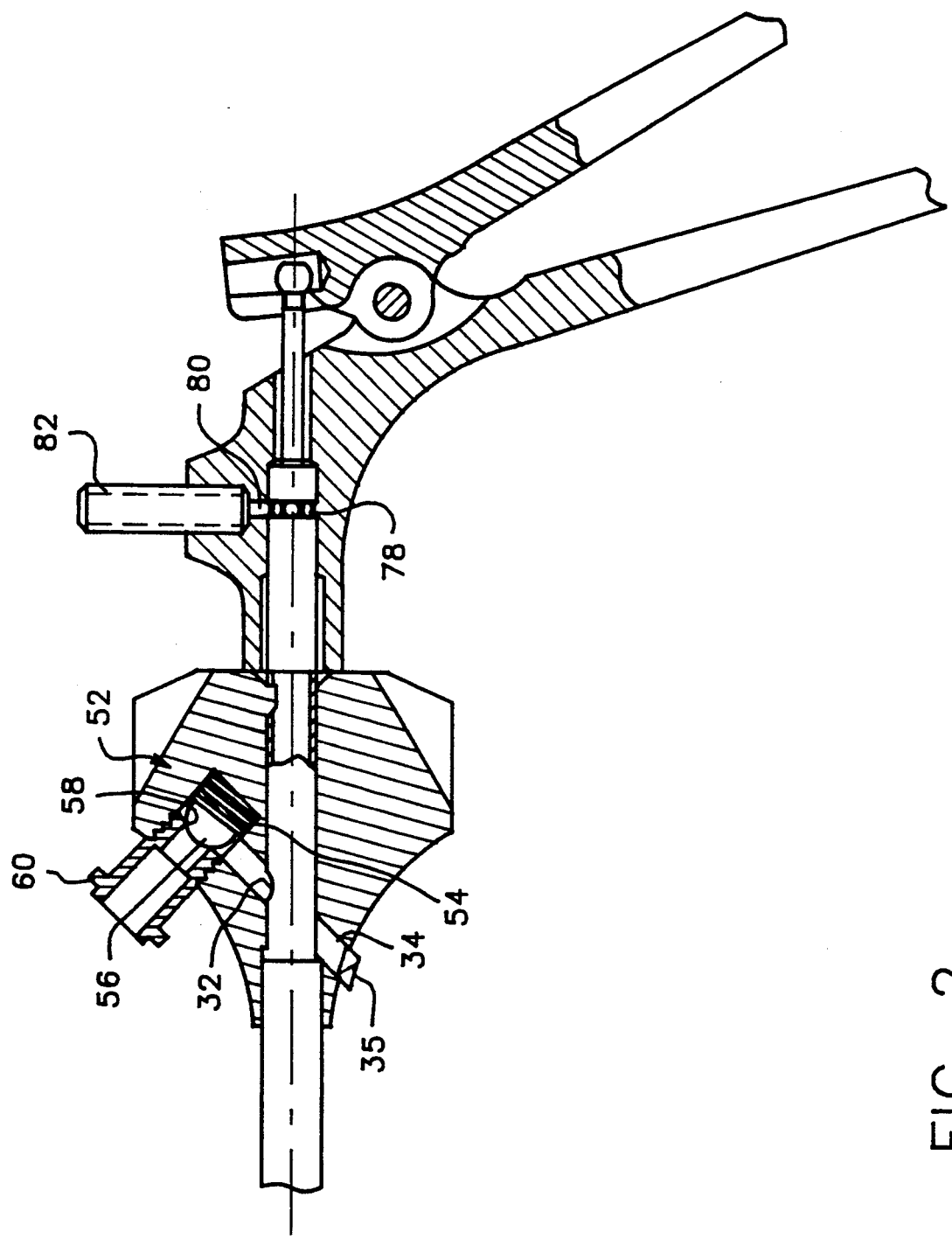
FIG. 2 is a detailed view of the proximal end of the instrument around the handle.

As previously stated, capture 46 has detents 76 thereon. As seen in FIG. 2, the detents 76 have hemispherical-shaped bottoms 78, into which a plunger 80 can extend. The hemispherical-shaped bottoms 78 are disposed at selected increments such that rotation of knob 24 will result in an audible click. The reason for that is that plunger housing 82 has an internal spring (not shown) which biases plunger 80 downwardly into detents 76. Since ball 20 is connected to recess 18 in a manner that permits rotation, such as in a ball and socket joint, the entire assembly beginning with knob 24, stem assembly 26, linkage 68, and with it jaws 72 and 74, back to rod 22, all the way back to ball 20, can rotate in unison with the combination of plunger 80 and detent 76, giving an audible sound or a feel to the apparatus A for the surgeon to know when a fixed amount of rotation has taken place. In the preferred embodiment, the hemispherical bottoms 78 are disposed at 45° intervals. Alternatively, plunger 80 and detents 76 can be eliminated if desired. With appropriate modifications that will be understood by those skilled in the art, the plunger housing 82 can also serve as a post for a monopolar cautery.

Those skilled in the art will appreciate that different mechanisms other than the jaw assembly can be placed at the distal end 30 of the apparatus A without departing from the spirit of the invention.

As presented, the apparatus A is simple to construct, economical to build, and provides several advantages to the surgeon doing an endoscopic procedure. First, the surgeon has the ability to ensure a thorough cleaning of the instrument between procedures using the flush mechanism described through fitting 60. Second, the apparatus A, through the use of the ball check assembly 52, retains internal pressures applied during the endoscopic procedure. No bulky valves are required, nor must the surgeon remove a cap in order to apply the flushing fluid. The use of the knob 24 allows simple rotation of the instrument mounted at the distal end 30 of the apparatus A. The plunger 80, in combination with detents 76, gives tactile and, if desired, audible indication of rotation of a fixed amount of degress. This assembly also helps to hold the position of an instrument at the distal end 30 of the apparatus A.

The foregoing disclosure and description of the invention are illustrative and explanatory thereof, and various changes in the size, shape and materials, as well as in the details of the illustrated construction, may be made without departing from the spirit of the invention.

We claim:

1. An endoscopic apparatus, comprising:
   a stem having a proximal end, a distal end, and an interior surface;
   a handle mounted to said proximal end of said stem;
   an instrument mounted to said distal end of said stem;
   operating means extending in said stem and defining an annulus therein to operably connect said handle to said instrument;
   seal means mounted internally of said stem in said annulus in contact with said interior surface thereof and circumscribing while sealing against said operating means, said seal means disposed adjacent said proximal end of said stem;
   access means in said stem for unidirectional introduction of pressurized fluid into said annulus, said seal means preventing exit of the pressurized fluid at said proximal end while forcing the fluid down said annulus toward the distal end of said stem for clean-out thereof, said access means preventing fluid flow out of said stem during an endoscopic procedure;
   said handle rotationally movable with respect to said seal means;
   said instrument, said stem, said operating means, and said access means selectively rotationally movable in tandem with respect to said handle.

2. The apparatus of claim 1, further comprising:
   indexing means on said handle responsive to rotational movement of said instrument to signal movements of predetermined angular intervals.

3. The apparatus of claim 2, wherein:
   said indexing means further retains a preselected angular position of said instrument until defeated by a predetermined torsional force applied to said stem.

4. The apparatus of claim 1, wherein:
   said access means further comprises a check valve.

5. The apparatus of claim 1, further comprising:
   a source of pressure connected to said access means for cleaning out said stem.

6. An endoscopic apparatus, comprising:
   a stem having a proximal end, a distal end, and an interior surface;
   a handle mounted to said proximal end of said stem;

an instrument mounted to said distal end of said stem;

operating means extending in said stem and defining an annulus therein to operably connect said handle to said instrument;

seal means mounted internally of said stem in said annulus in contact with said interior surface thereof and circumscribing while sealing against said operating means, said seal means disposed adjacent said proximal end of said stem;

access means in said stem for unidirectional introduction of pressurized fluid into said annulus, said seal means preventing exit of the pressurized fluid at said proximal end while forcing the fluid down said annulus toward the distal end of said stem for clean-out thereof, said access means preventing fluid flow out of said stem during an endoscopic procedure;

a detent member mounted to said operating means, said detent member having a plurality of detent positions circumferentially displaced from each other;

a plunger mounted to said handle biased into engagement of said detent positions;

whereupon application of a predetermined rotational force to said stem, which results in tandem movement of said instrument, said biased plunger is displaced from extension into one of said detent positions until sufficient stem rotation allows said plunger to engage an adjacent said detent position.

7. An endoscopic apparatus, comprising:

a stem having a proximal end and a distal end;

instrument means for performing an endoscopic procedure mounted adjacent to said distal end of said stem;

actuating means extending through said stem to said instrument and operable from said proximal end of said stem for selective operation of said instrument means;

said actuating means defining an annular passage within said stem;

grip means movably mounted adjacent said proximal end of said stem, said grip means operably connected to said actuating means for holding the endoscopic apparatus and for selective operation of said actuating means;

said instrument means mounted movably with respect to said grip means for selective reorientation of said instrument means and said grip means during an endoscopic procedure;

said actuating means being pivotally mounted to said grip means to allow said actuating means to rotate with said instrument means for repositioning thereof;

access means mounted to said stem for allowing access into said stem, said access means selectively capable of remaining stationary relative to rotational movement of said grip means;

said access means selectively movable in tandem with said stem;

sealing means in said stem mounted proximally of said access means;

said access means facilitating fluid communication into said annular passage distally of said sealing means for cleaning out said annular passage with fluid pressure;

said access means further comprising:

a check valve to allow fluid ingress to flush said annular passage and to retain pressures present in said annular passage during the endoscopic procedure.

8. The apparatus of claim 7, wherein said sealing means further comprises:

an annular backup member mounted to said stem;

an annular sealing member mounted adjacent said backup member;

a capture member connected to said stem, said capture member squeezing said sealing member against said backup member to seal off said annular passage against said stem and said actuating means, said actuating means extending through said backup, sealing, and capture members.

9. An endoscopic apparatus having a proximal and distal end, comprising:

a handle;

a pair of working elements situated at said distal end of said apparatus;

an outer cylindrical sleeve mounted to said handle;

an inner activating rod mounted to said handle and axially movable within said outer sleeve, said inner rod adapted to operate said working elements in response to movement of said handle;

means on said sleeve for rotating said inner rod in tandem with said outer sleeve;

said means for rotating comprising a cylindrical knob concentrically secured to said outer sleeve;

means on said sleeve for providing access to the interior of said outer sleeve for fluid cleaning;

sealing means for selectively sealing said means for providing access;

said handle rotationally movable with respect to said means for providing access; and said sleeve, rod, and means for providing access selectively rotationally movable in tandem with respect to said handle.

10. The apparatus of claim 9, further comprising:

a check valve interposed within said means for providing access said check valve adapted to enable fluid communication between the exterior of said instrument and the interior of said sleeve in response to a predetermined fluid pressure.

11. An endoscopic apparatus, comprising:

a stem having a proximal end and a distal end;

instrument means for performing an endoscopic procedure mounted adjacent to said distal end of said stem;

actuating means extending through said stem to said instrument and operable from said proximal end of said stem for selective operation of said instrument means;

said actuating means defining an annular passage within said stem;

grip means movable mounted adjacent said proximal end of said stem, said grip means operably connected to said actuating means for holding the endoscopic apparatus and for selective operation of said actuating means;

said instrument means mounted movable with respect to said grip means for selective reorientation between said instrument means and said grip means during an endoscopic procedure;

said actuating means is pivotally mounted to said grip means to allow said actuating means to rotate with said instrument means for a repositioning thereof;

sealing means in said annular passage mounted to said stem;

port means for facilitating fluid communication into said annular passage distally of said sealing means for cleaning out said annular passage with fluid pressure, said sealing means mounted proximally of said port means and between said handle and said port means;

said sealing means further comprises:
an annular backup member mounted to said stem;
a sealing member mounted adjacent said backup member;
an annular capture member connected to said stem, said capture member squeezing said sealing member against said backup member to seal off said annular passage against said stem and said actuating means, said actuating means extending through said backup, sealing, and capture member;
said capture member has a plurality of detent positions thereon;
said group means further comprising a biased plunger selectively engagable with said detent positions on application of a rotational force to said capture member; and
said port means further comprising a check valve to allow fluid ingress to flush said annular passage and to retain pressure present in said annular passage during the endoscopic procedure.

12. The apparatus of claim 11, wherein:
said actuating means translates and rotates on its axis with respect to said backup and sealing members;
whereupon rotational force applied to said stem results in rotation of said instrument means, said actuating means, and said capture member, displacing said plunger from one of said detent positions into another.

13. The apparatus of claim 12, wherein:
said displacement of said plunger from one detent position to another gives an audible sound indicative of rotational movement.

14. An endoscopic apparatus, comprising:
a stem having a proximal end, a distal end, and an interior surface;
a handle mounted to said proximal end of said stem;
an instrument mounted to said distal end of said stem;
said stem and said instrument are operably connected for tandem rotational movement with respect to said handle to facilitate positioning of said instrument during an endoscopic procedure;
operating means extending in said stem and defining an annulus therein to operably connect said handle to said instrument;
said operating means and said instrument are rotatable in tandem with respect to said handle in response to a rotational force applied to said stem for positioning of said instrument during endoscopic procedures;
seal means mounted internally of said stem in said annulus in contact with said interior surface thereof and circumscribing while sealing against said operating means, said seal means disposed adjacent said proximal end of said stem;
access means in said stem for unidirectional introduction of pressurized fluid into said annulus, said seal means preventing exit of the pressurized fluid at said proximal end while forcing the fluid down said annulus toward the distal end of said stem for clean-out thereof, said access means preventing fluid flow out of said stem during an endoscopic procedure;
indexing means on said handle responsive to rotational movement of said instrument to signal movements of predetermined angular intervals;
said indexing means further retains a preselected angular position of said instrument until defeated by a predetermined torsional force applied to said stem;
said indexing means further comprises:
a detent member mounted to said operating means, said detent member having a plurality of detent positions circumferentially displaced from each other;
a plunger mounted to said handle biased into engagement of said detent positions;
whereupon application of a predetermined rotational force to said stem biased plunger is displaced from extension into one of said detent positions until sufficient stem rotation allows said plunger to engage an adjacent said detent position.

* * * * *